United States Patent [19] [11] 4,227,886
Bullock et al. [45] Oct. 14, 1980

[54] TESTING A CUVETTE FOR CLEANLINESS

[75] Inventors: David G. Bullock; Roger A. Bunce; Ian R. Clark, all of Birmingham, England; Ian D. Duff, Ossining, N.Y.; Geoffrey S. Greaves, Droitwich, England; Peter H. Lloyd, Birmingham, England; Ann M. Peters, Birmingham, England; Thomas P. Whitehead, Leamington Spa, England; Peter Wilding, Birmingham, England

[73] Assignee: National Research Development Corporation, London, England

[21] Appl. No.: 796,612

[22] Filed: May 13, 1977

[30] Foreign Application Priority Data

May 13, 1976 [GB] United Kingdom ............... 19850/76
May 3, 1977 [GB] United Kingdom ............... 19850/77

[51] Int. Cl.² .......................... B08B 7/00; B08B 5/04; G01N 29/02
[52] U.S. Cl. .................................. 23/230 R; 134/25.2; 134/18; 134/21; 134/22 R; 134/81; 134/113; 134/152; 422/64; 356/240
[58] Field of Search .............. 134/18, 22 R, 24, 25 A, 134/42, 21, 80, 81, 113, 152, 171; 209/111.7 R; 23/272 SC, 259; 250/223 B, 341; 356/237, 240

[56] References Cited

U.S. PATENT DOCUMENTS

| 2,296,027 | 9/1942 | Gettelman ............................ 356/240 |
| 3,217,877 | 11/1965 | Honjyo et al. ..................... 209/111.7 |
| 3,364,811 | 1/1968 | Baruch et al. ............................ 88/14 |
| 3,417,241 | 12/1968 | Davis ...................................... 134/42 |
| 3,421,840 | 1/1969 | Pechmann ............................... 134/24 |
| 3,528,544 | 9/1970 | Noguchi et al. ................... 209/111.7 |
| 3,684,452 | 8/1972 | Bessman .......................... 23/272 SC |
| 4,066,412 | 1/1978 | Johnson et al. ........................ 23/259 |

FOREIGN PATENT DOCUMENTS

| 2206054 | 8/1973 | Fed. Rep. of Germany ........... 356/240 |
| 1401426 | 7/1975 | United Kingdom ..................... 134/113 |

Primary Examiner—Joseph Scovronek
Assistant Examiner—Chris Konkol
Attorney, Agent, or Firm—Cushman, Darby & Cushman

[57] ABSTRACT

In testing for cleanliness a cuvette having translucent wall portions, the cuvette is preferably partially filled with pure water and then a beam of optical radiation is directed at a said wall portion, the intensity of radiation which has passed through the cuvette by direct transmission or by scattering is detected, and the state of cleanliness of the cuvette is determined from a comparison between the detected optical intensity and a criterion indicative of cuvette cleanliness.

The invention finds particular application to testing cuvettes for cleanliness which have been washed in a laundry of an automatic blood analysing machine.

16 Claims, 7 Drawing Figures

TESTING A CUVETTE FOR CLEANLINESS

This invention relates to testing a cuvette for cleanliness.

According to one aspect of the invention there is provided a method of testing for cleanliness a cuvette having translucent wall portions, wherein a beam of optical radiation is directed at a said wall portion of the cuvette, radiation which has passed through the cuvette is investigated, and the state of cleanliness of the cuvette is determined from the investigated radiation.

By "optical" is meant radiation of wavelength greater than X-rays but less than microwaves, i.e. including infra-red and ultra-violet radiation as well as visible radiation.

Preferably, in use, the cuvette is at least partially filled with a "reference" liquid (pure water or alcohol), the beam of radiation is directed at the "reference" liquid in the cuvette, and radiation which has passed through the "reference" liquid is investigated. The radiation may pass through the cuvette by direct transmission, or radiation which has been scattered from the cuvette is investigated.

According to another aspect of the invention there is provided apparatus for testing for cleanliness a cuvette having translucent wall portions, the apparatus comprising means for directing a beam of optical radiation at a said wall portion, radiation investigating means for investigating optical radiation which has passed through the cuvette, and computer means arranged, in use, to change a state thereof in response to the investigated radiation indicating that the cuvette does not comply with a criterion of cuvette cleanliness.

In the preferred construction, the apparatus comprises a source of "reference" liquid (pure water or alcohol) and means for at least partially filling the cuvette with such "reference" liquid from the source, the radiation directing means being arranged to direct the beam of optical radiation at the "reference" liquid in the cuvette and the radiation investigating means being arranged to investigate optical radiation which has passed through the "reference" liquid.

For a better understanding of the invention and to show how the same may be carried into effect, reference will now be made, by way of example, to the accompanying drawings, in which.

Figure 1:
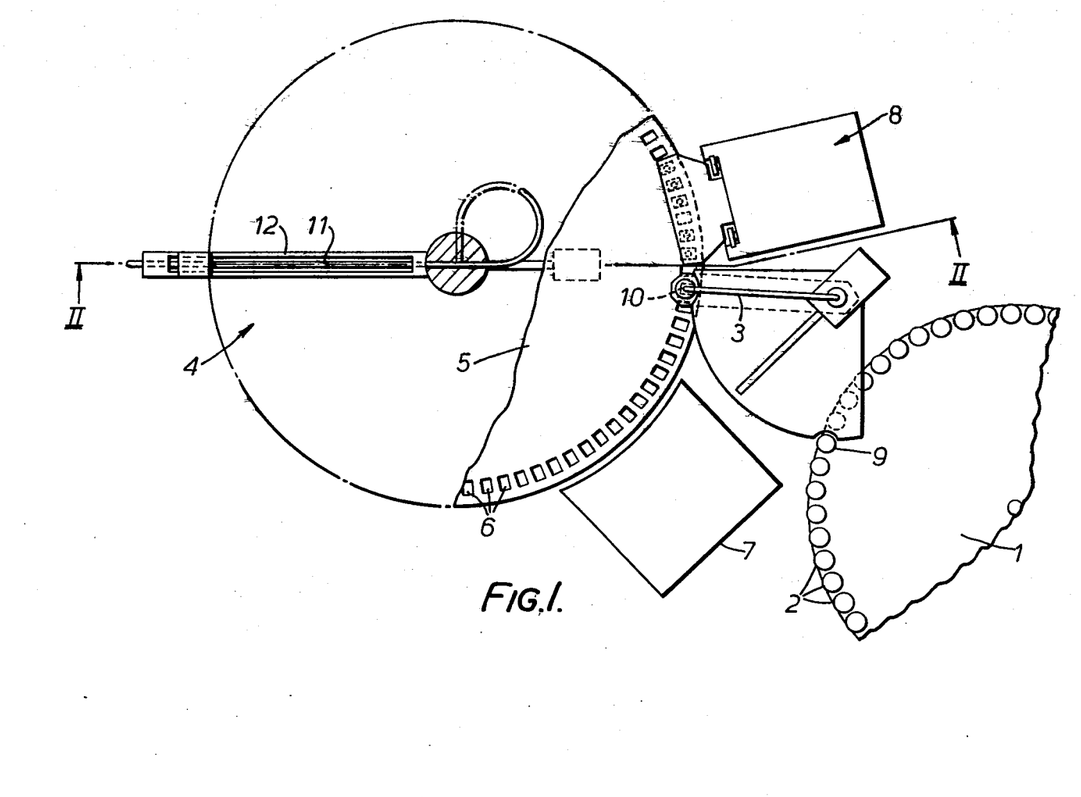
FIG. 1 is a view of apparatus forming part of an automatic blood analysing machine, the view being taken along the line I—I of FIG. 2 with the cover of the apparatus removed.
Figure 2:
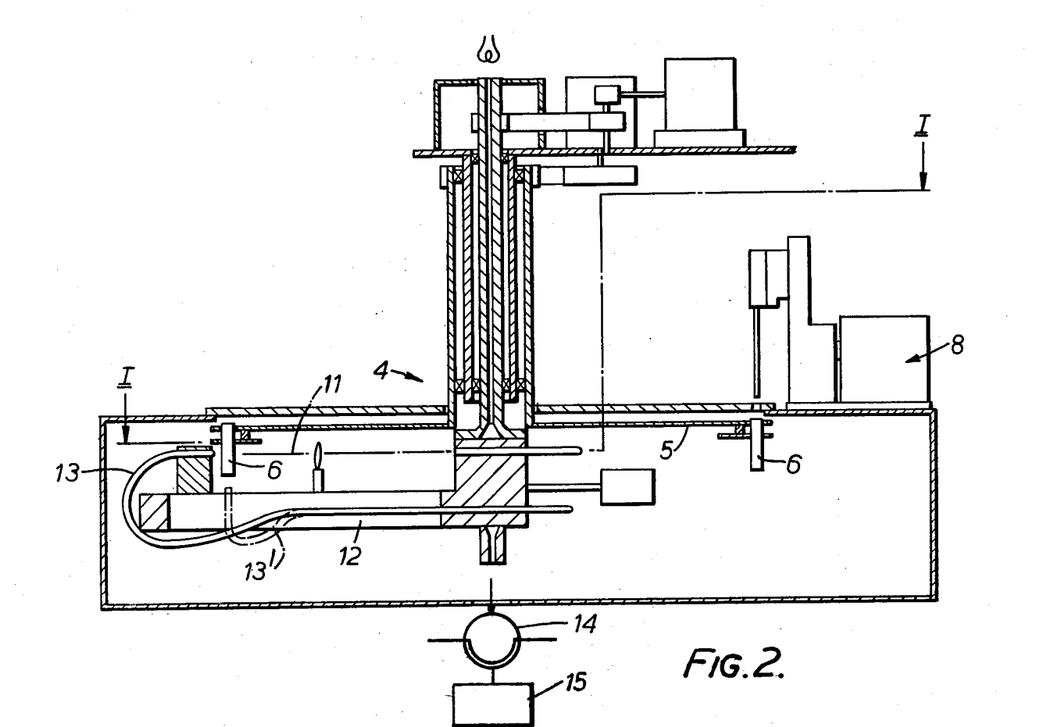
FIG. 2 is a vertical sectional view of the apparatus taken along the line II—II of FIG. 1.

The apparatus shown in FIGS. 1 and 2 comprises essentially firstly a turntable 1 formed around its periphery with pockets accommodating vials 2 containing various serums to be analysed, secondly a sample transfer head 3, thirdly apparatus 4 for carrying out colorimetric, fluorimetric or light-scattering analyses of samples, the apparatus 4 including a turntable 5 bearing cuvettes 6 which are situated in its peripheral region and into which serum samples are discharged for analysis from the vials by the transfer head 3, fourthly a station 7 in which reagents, and possibly diluents also, are added to the serum samples in the cuvettes 6, and lastly a laundry 8 where the cuvettes are discharged of their contents, washed, tested for cleanliness and then dried before being re-charged with further serum samples. The combination of the turntable 1 and vials 2 forms the subject of U.S. Pat. No. 4,056,361 and the apparatus 4 is disclosed in U.S. Pat. No. 3,966,322.

Reference is directed to the above two prior patents for a full disclosure of how the turntable 1 and apparatus 4 are constructed and operate, but for the present purposes a brief account of operation of the blood analysing machine will now be given.

In use, both turntables 1 and 5 are rotated stepwise and in synchronism with one another. Considering a given vial 2, this is advanced stepwise by the turntable 1 until the vial arrives at the position 9 where, during a rest period of the turntables, the transfer head transfers a measured quantity of serum in that vial to the cuvette 6 at position 10. This cuvette is advanced stepwise to the station 7 where, during another dwell period, a predetermined quantity of reagent, and possibly diluent too, is dispensed into the cuvette and a chemical reaction commences between the serum and reagent. Between this time and the time when the cuvette 6 arrives at the laundry 8, the reaction products in the cuvette are scanned at least once during each dwell period of the turntable 5 by a circularly scanning, radial beam of light directed along an axis 11 by a fibre-optic optical system incorporated in a rotary assembly, rotating at constant speed and including an arm 12. Light which is transmitted through the cuvette and reaction products (or scattered downwardly by the reaction products) enters a fibre optic guide 13 (or 13') which directs the light to a photomultiplier 14 which provides an output signal whose magnitude depends upon the intensity of the light received by the guide 13 (or 13'). The output signal is fed to a computer 15 which stores data in respect of the cuvette 6 (and the other cuvettes too) for each revolution of the arm 12, the computer only accepting signals from the photomultiplier tube when the turntable 5 is at rest.

When the cuvette 6 arrives at the laundry 8, the reaction products are removed, the cuvette washed, tested for cleanliness and finally dried, following which the cuvette is ready for the next serum sample to be discharged into it by the transfer head 3. The construction of the laundry 8 will now be described in detail with reference to FIG. 3 to 6.

Figure 3:
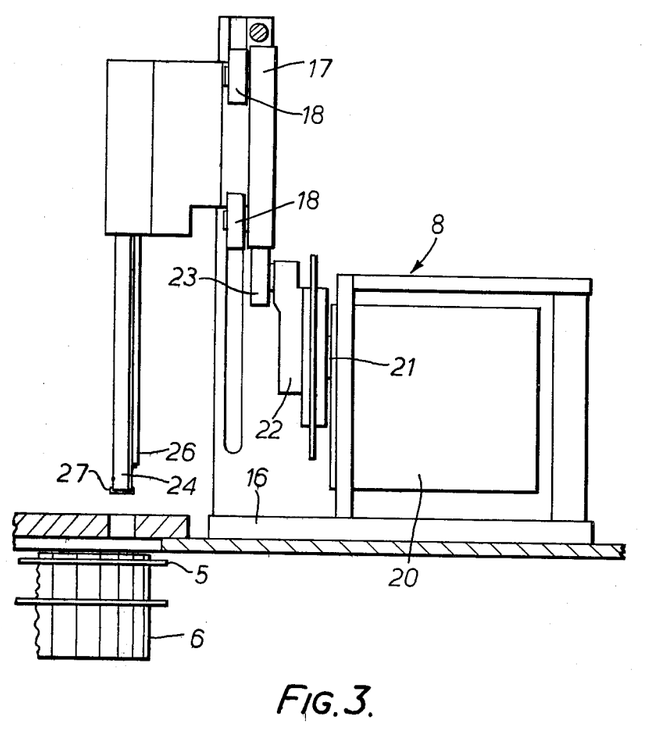
FIG. 3 is a view on an enlarged scale of part of FIG. 2 showing a laundry in side elevation with part of the side of the laundry removed to expose a carriage and its wheels.
Figure 4:
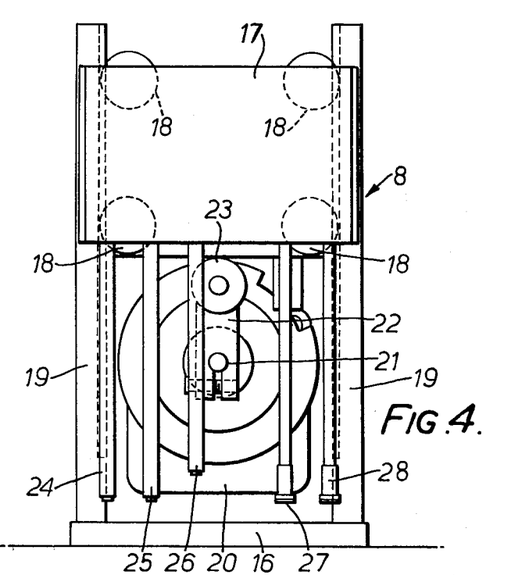
FIGS. 4 and 5 are respectively a front elevation and a plan view of the laundry of FIG. 3.
Figure 5:
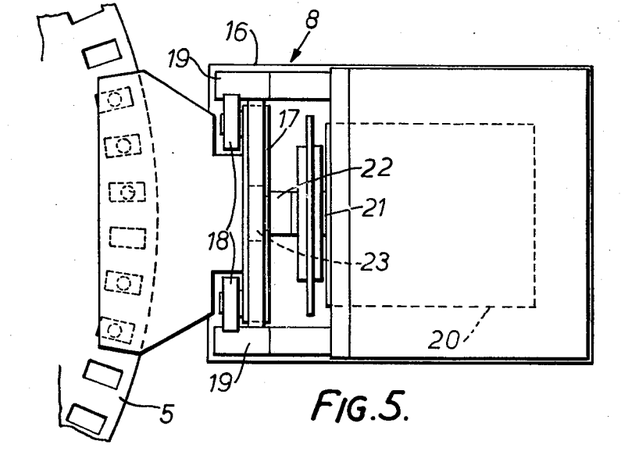

The laundry 8 comprises a support frame 16 and a carriage 17 which is vertically movable in the frame by means of wheels 18 on the carriage which run on vertical rails 19 of the frame 16. Mounted on the base of the frame 16 is an electric motor 20 to the shaft 21 of which is secured a crank 22. A roller 23 is mounted on the end of this crank and the lower, horizontal edge surface of the carriage 17 rests on this roller.

In order to lower the carriage from its uppermost position illustrated in FIGS. 3 and 4, the motor 20 is operated to rotate its shaft through a half revolution to bring the roller 23 to its lowermost position. The carriage thereby lowers itself under its own weight to its lowermost position. By rotating the motor shaft through a half revolution again, the roller 23 runs along the bottom edge surface of the carriage to raise it again into its uppermost position.

Extending downwardly from the carriage, starting from the left in FIG. 4, are a first washing probe 24, a second washing probe 25 spaced from the probe 24 by a distance equal to the spacing between adjacent cuvettes in the turntable 5, a dispensing probe 26 at the same spacing from the probe 25 as the cuvette spacing, a first plunger probe 27 spaced from the probe 26 by a distance equal to twice the cuvette spacing, and lastly a second plunger probe 28 at an equal spacing from the probe 27 to the cuvette spacing. In the lowermost position of the carriage, all the probes 24 and 28 are positioned in respective cuvettes 6 in the turntable 5 and when the carriage is fully raised, the lower ends of the probes are clear of the tops of the cuvettes so that the turntable 5 can be indexed into the next position.

Figure 6:
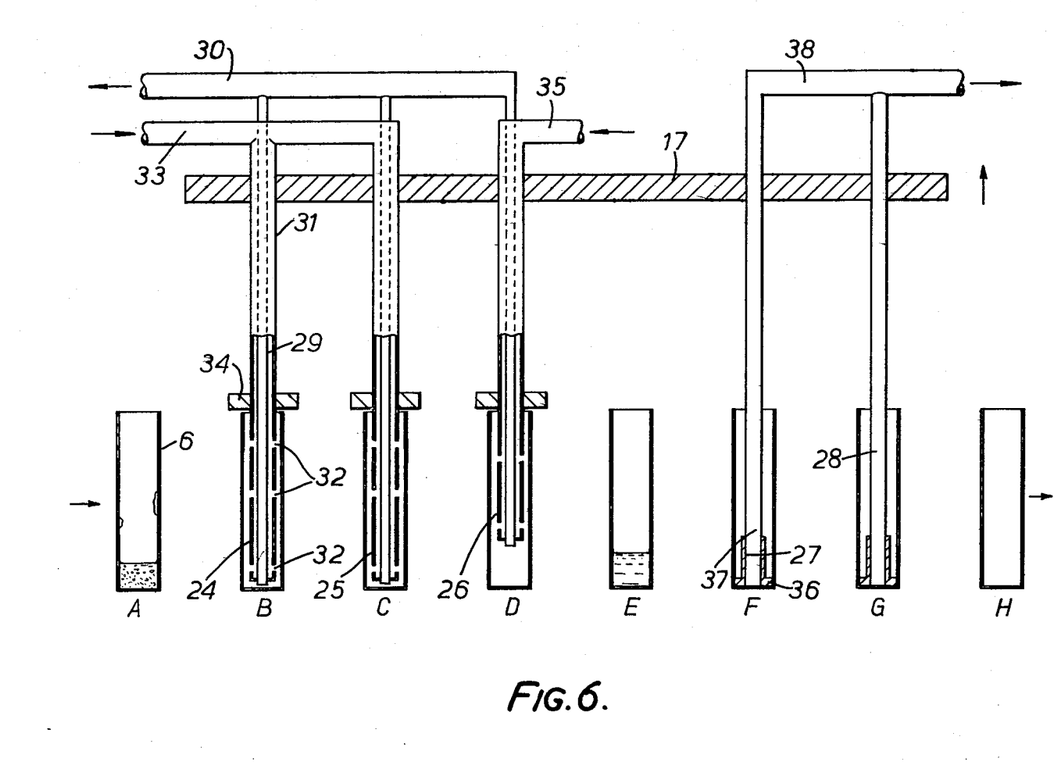
FIG. 6 is a diagrammatic front view of the laundry.

Considering the progress of a cuvette 6 through the laundry, a cuvette is indexed from position A (see FIG. 6) in one stepwise rotation of the turntable 5 into position at a first position B of the laundry while the carriage 17 is held in its raised position. At this station, the carriage is lowered and the washing probe is lowered to the bottom of the stationary cuvette. As can be seen in FIG. 6 the probe 24 comprising a concentric tube arrangement of which the inner tube 29 is connected to a vacuum line 30 and the outer tube 31, which is blanked off at its lower end and provided in its wall with three axially spaced apart sets of radially directed jets 32, is supplied with tap water by a supply line 33. This water may contain detergent for improved washing-out. The water issuing from the jets runs down the side walls of the cuvette, and the water and washed down residues from the inner surfaces of the cuvette are sucked up by the vacuum line 30.

To prevent wash water splashing out of the top of the cuvette due to impact with its sides, the outer tube 31 is provided with an anti-splash collar 34. The lower surface of each terminates just above the top of the cuvette, so that there is a high velocity air flow directed across the top surface of, and down into, the cuvette. Any air-borne droplets are thus directed back down into the cuvette.

The carriage is then raised to allow the cuvette to be advanced to its next position at a second station C where the washing probe 25, which is identical to the probe 24, repeats exactly the above-described operation to increase the washing efficiency and minimize the chances of the washed cuvette not reaching a predetermined standard of cleanliness.

In order to test the cleanliness of the cuvette, a dispensing probe similar to the washing probes is lowered into the cuvette after it has been advanced from the station C to a third station D, and this time pure water (i.e. distilled or deionised) from a pure water supply line 35 is pumped into the cuvette while the central tube of the concentric tube arrangement which is connected to the vacuum line 30 sucks any remaining tap water and excess pure water from the cuvette. It will be noticed in FIG. 6 that the lower end of the dispensing probe 26 is spaced away from the bottom of the cuvette in the lower-most position of the carriage 17 so that when the carriage is next raised, a predetermined quantity of pure water remains in the cuvette. After the next rotational step has been completed the cuvette comes to rest at a station E.

The circularly scanning beam of light scans the cuvette as its passes through the laundry 8. Light which has passed through the pure water in the cuvette at the fourth station E, either by direct transmission or by light-scattering, is detected and investigated, as described above. From data stored in the computer, the state of cleanliness of the cuvette is determined.

In the next rotational advance of the turntable 5, the cuvette is brought to a fifth station F where the plunger probe 27 is lowered by the carriage into the cuvette, the probe comprising a plunger 36 arranged at the lower end of an upright tube 37 connected to another vacuum line 38 so as to suck the pure water from the cuvette. As the plunger enters the cuvette, any pure water on the inner wall surfaces of the cuvette is forced down by the plunger to the bottom of the cuvette, there being diagonal grooves formed in the underside surface of the plunger so that pure water drawn down to the cuvette bottom can be sucked out. The cuvette is then indexed into position at a sixth station G where the plunger probe 28, identical to the plunger probe 27, is lowered into the cuvette to remove any remaining traces of pure water. Finally, after the next rotational step of the turntable 5, the cuvette, at position H, is clean and dry and ready to have another serum sample dispensed into it for analysis.

The computer 15 may be used for controlling operation of the various pumps and drive motors required to cause the laundry to operate in the manner described. A preferred manner of controlling the laundry will now be described with reference to FIG. 7.

Figure 7:
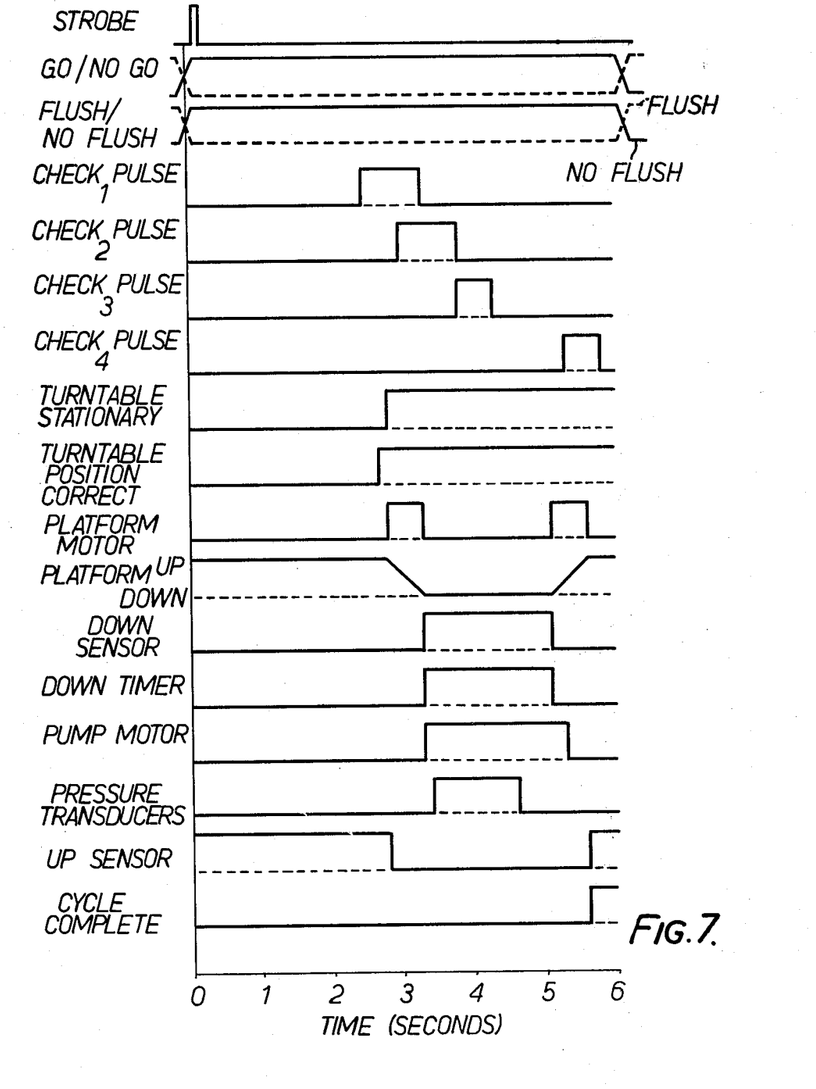
FIG. 7 is a timing diagram illustrating operation of the laundry.

In this system, a two bit command generated by the computer is used, the command word being go/not go and flush/not flush. A strobe pulse sets the point in time at which the two bit command is generated. A control device responsive to the command word is arranged to generate control pulses enabling the above described operations to be carried out.

A 'go' pulse is produced by the computer and the control device accordingly generates four check signals which serve to check that the required operations are carried out as will be described hereinbelow.

The turntable 5 should become stationary during the period of check signal 1. A signal is provided when the turntable is stationary and another signal is produced to provide an indication that the turntable is positioned with the cuvettes directly below the probes 24 to 28. Assuming these latter two signals occur simultaneously during the period of check signal 1, the washing operations will commence. If the stated condition does not occur, an error code is generated. The washing operations are brought about by the electric motor 20 operating so as to allow the carriage to be lowered under its own weight, thus introducing the probes 24 to 28 into the cuvettes 6. The carriage should reach its lowest extent of travel, determined by a 'down' sensor, in the period defined by check pulse 2. If this is not the case the motor 20 is arranged to continue to run until an 'up' sensor, for determining when the carriage 17 is fully raised, is activated an an error signal generated. With the carriage in its lowermost position, the 'down' sensor operates water pump motors in the tap and pure water lines, assuming the 'flush' command has been received by the control device. The water pumps can be so constructed and arranged that a single revolution performed by each pump will supply the required quantity of water. The water pump motor circuit of each pump is arranged with a view to ensuring that once triggered the pump performs a complete revolution and then stops in preparation for the next cycle of operations. The 'down' sensor also starts off a down timer. If the 'flush' command had not been received, the carriage drive motor 20 is arranged to start again at the end of the timer down period, whatever the circumstances. On the other hand, however, assuming that the 'flush' command has been received at the appropriate time, the control device checks that two pressure transducers, fitted respectively in the common tap water supply line and the pure water line between the pumps and the washing probes and responsive to water pressures above a predetermined value, are giving an output for the duration of check pulse 3. If not, an error signal is generated (for instance to indicate 'no water'). The control device also checks that the transducer signals are not present at the end of the down timer signal. If they were, this is likely to be due to air bubbles which are present causing an excessively-long-duration water jetting to occur. If all is well, the carriage drive motor 20 is actuated. If not, another error signal is generated and the electric motor 20 is not actuated until the offending transducer switches off. When the carriage reaches its fully 'up' position, its drive motor 20 is stopped by the 'up' sensor regardless of the previous operating sequence. The 'up' signal and check signal 4 are tested for coincidence and if this is detected a cycle complete signal is generated.

The various error signals may be used to provide a visual or audible indication of the nature of the faulty operation.

Several additional safety features should preferably be incorporated, e.g.:

(1) The cuvette washing system should not be able to operate without the vacuum lines being operative.

(2) The system should reset itself automatically upon switch-on and should be provided with a master reset facility.

(3) An interlock should be provided to prevent the turntable 5 stepping unless the probe support is in its 'up' position.

It is proposed that the vacuum be applied continuously, thus eliminating the need for further timing circuitry and also the possibility of any water droplets being left in the washed cuvette.

Generally, it is anticipated that the washed cuvette will be sufficiently clean to meet prespecified cleanliness requirements. However, the detected intensity of light received from the cuvettes may indicate that a washed cuvette is not sufficiently clean. The computer may be arranged, in that event, to prevent dispensing of the next serum sample and, subsequently, reagent and diluent into the cuvette. However, when the turntable has completed a full rotation, the cuvette will be rewashed in the laundry and then checked again for cleanliness. Alternatively, another serum sample and reagent and diluent may be dispensed into that cuvette, but the computer is then arranged to disregard the data received for that cuvette so long as it does not satisfy the cleanliness criterion.

The wavelength of the optical radiation will generally be selected in dependance upon the reaction mixture in the cuvette so as to obtain maximum sensitivity from the apparatus.

Various ways are possible for determining the state of cleanliness of each cuvette. For example, the determination may be made by comparison with the reading obtained on the passage of the cuvette through the cuvette cleaner during the previous cycle of the turntable (assuming that the cuvette was clean then), by reference to predetermined limit values (which may be specific to each cuvette) between which the reading will lie if the cuvette is sufficiently clean, by separate comparisons of absolute readings obtained at differnt wavelengths with respective reference readings, by comparing difference readings between the various readings obtained at different wavelengths with respective reference difference readings, or by a combination of these techniques.

Instead of distilled water, alcohol could be used as the "reference" liquid when the cuvette is tested for cleanliness. Moreover, it is not essential that a "reference" liquid be dispensed into each cuvette for use in determining whether or not it is sufficiently clean. Indeed, it is possible, although less desirable, to direct radiation at an empty cuvette. Any remaining traces of reaction products on the walls of the cuvette will affect the optical properties of the cuvette so that its state of cleanliness may be determined from the detected intensity of scattered or directly transmitted light.

We claim:

1. Apparatus for use in analyzing specimens, said apparatus comprising:
   a carrier having mounted thereon a plurality of cuvettes for containing specimens to be analyzed;
   means for advancing the carrier to cause each cuvette to pass repeatedly through, in succession, a specimen loading region, an analysis region, a cleaning region, and a cleanliness testing region;
   means for introducing specimens into said cuvettes while they are located in the specimen loading region;
   means for performing an analytical test on the specimens in the cuvettes in the analysis region;
   means for cleaning the cuvettes when located in the cleaning region;
   means for effecting a cleanliness test on the cuvettes when they are located in the cleanliness testing region; and
   means operative during the continued advancement in said succession of a specified cuvette, which fails the cleanliness test but is retained on said carrier, for inhibiting the effective use of said specific cuvette until it is tested favorably by said testing means following at least one further cleaning of that specific cuvette by said cleaning means.

2. Apparatus according to claim 1, wherein said analytical testing means comprises means for performing a test on the optical characteristics of the specimens.

3. Apparatus according to claim 2 wherein the cuvettes are mounted on the carrier in a series so that the cuvettes are advanced one-by-one through the successive regions, and the optical characteristics testing means includes an optical scanner for scanning the specimens in the analysis region a number of times.

4. Apparatus according to claim 2, wherein the carrier is a turntable having the cuvettes mounted thereon in a circular array centered on the axis of rotation of the turntable, and the optical characteristics testing means includes an optical scanner mounted for rotation about said axis of rotation.

5. Apparatus according to claim 1, wherein said cleanliness testing means comprises means for performing a test on the optical characteristics of the cuvettes.

6. Apparatus according to claim 1, wherein said inhibiting means comprises means to inhibit operation of the specimen introducing means in respect of the specific cuvette which has failed the cleanliness test.

7. Apparatus according to claim 1, wherein said cleanliness testing means comprises means to effect the cleanliness test by comparing test data obtained in respect of each cuvette at said cleanliness testing region with data obtained at said region the previous time for the same cuvette.

8. Apparatus according to claim 5 and further comprising:
means in the cleanliness testing region operative to introduce into the cuvettes prior to the cleanliness test a liquid having optically uniform properties; and
means also in the cleanliness testing region for removing this liquid from the cuvettes after the cleanliness test.

9. A method of analyzing specimens contained in a plurality of cuvettes mounted on a carrier, said method comprising:
advancing the carrier to cause each cuvette to pass repeatedly through, in succession, a specimen loading region, an analysis region, a cleaning region, and a cleanliness testing region;
introducing specimens into said cuvettes while they are located in the specimen loading region;
performing an analytical test on the specimens in the cuvettes in the analysis region;
cleaning the cuvettes when they are located in the cleaning region;
effecting a cleanliness test on the cuvettes when they are located in the cleanliness testing region; and
inhibiting the effective use of a specific cuvette which fails the cleanliness test until it is tested favorably following at least one further cleaning during its continued advancement on said carrier and in said succession into said cleaning and testing regions.

10. A method according to claim 9, wherein said analytical test comprises performing a test on the optical characteristics of the specimens.

11. A method according to claim 10, wherein the cuvettes are mounted on the carrier in a series so that the cuvettes are advanced one-by-one through the successive regions, and the operation of performing the analytical test includes optically scanning the specimens in the analysis region a number of times.

12. A method according to claim 10, wherein the carrier is rotated about an axis of rotation with the cuvettes mounted on the carrier in a circular array centered on the axis, and the operation of performing the analytical test includes optically scanning the specimens about said axis of rotation.

13. A method according to claim 9, wherein said operation of effecting a cleanliness test comprises performing a test on the optical characteristics of the cuvettes.

14. A method according to claim 9, wherein the operation of inhibiting the effective use of a specific cuvette which fails the cleanliness test comprises preventing introduction of specimen into that cuvette.

15. A method according to claim 9, wherein said operation of effecting a cleanliness test comprises comparing test data obtained with respect to each cuvette at said cleanliness testing region with data obtained at said region the previous time for the same cuvette.

16. A method according to claim 13, said method further comprising:
introducing a liquid having optically uniform properties into the cuvettes in the cleanliness testing region, prior to the cleanliness test; and
removing this liquid from the cuvettes in the cleanliness testing region, after the cleanliness test.

* * * * *

UNITED STATES PATENT AND TRADEMARK OFFICE
CERTIFICATE OF CORRECTION

PATENT NO. : 4,227,886
DATED : October 14, 1980
INVENTOR(S) : David G. BULLOCK et al It is certified that error appears in the above—identified patent and that said Letters Patent is hereby corrected as shown below:

In the heading

In: Foreign Application Priority Data
read second line as:
May 3, 1977 [GB]   United Kingdom...19850/76

Column 3, line 14, read "and" as --to--
Column 3, line 22, read "position" as --station--
Column 3, line 40, read "each terminates" as --each collar terminates--
Column 4, line 60, read "an an" as --and an--
Column 5, line 53, read "the" (first instance) as --that--
Column 6, line 6, read "differnt" as --different--

Signed and Sealed this

Twenty-first Day of April 1981

[SEAL]

Attest:

RENE D. TEGTMEYER

Attesting Officer    Acting Commissioner of Patents and Trademarks